United States Patent
Naor et al.

(10) Patent No.: US 9,358,099 B2
(45) Date of Patent: Jun. 7, 2016

(54) METHOD OF IMPLANTING A STENT GRAFT AND CREATING A FENESTRATION THEREIN

(75) Inventors: Gil Naor, Hofit (IL); Haim Ackerman, Caesarea (IL)

(73) Assignee: BIFLOW Medical Ltd., Nazaret-Elit (IL)

( * ) Notice: Subject to any disclaimer, the term of this patent is extended or adjusted under 35 U.S.C. 154(b) by 502 days.

(21) Appl. No.: 13/483,440

(22) Filed: May 30, 2012

(65) Prior Publication Data

US 2012/0239132 A1  Sep. 20, 2012

Related U.S. Application Data

(63) Continuation-in-part of application No. PCT/IL2010/001001, filed on Nov. 30, 2010.

(60) Provisional application No. 61/264,843, filed on Nov. 30, 2009, provisional application No. 61/524,123, filed on Aug. 16, 2011.

(51) Int. Cl.
| | |
|---|---|
| A61F 2/852 | (2013.01) |
| A61F 2/07 | (2013.01) |
| A61F 2/954 | (2013.01) |
| A61F 2/06 | (2013.01) |
| A61F 2/856 | (2013.01) |
| A61F 2/848 | (2013.01) |
| A61F 2/82 | (2013.01) |
| A61F 2/90 | (2013.01) |

(52) U.S. Cl.
CPC . *A61F 2/07* (2013.01); *A61F 2/954* (2013.01); *A61F 2/064* (2013.01); *A61F 2/852* (2013.01); *A61F 2/856* (2013.01); *A61F 2/90* (2013.01); *A61F 2002/061* (2013.01); *A61F 2002/067* (2013.01); *A61F 2002/821* (2013.01); *A61F 2002/826* (2013.01); *A61F 2002/828* (2013.01); *A61F 2002/8483* (2013.01); *A61F 2002/8486* (2013.01); *A61F 2220/0016* (2013.01); *A61F 2220/0091* (2013.01); *A61F 2230/0086* (2013.01); *A61F 2230/0093* (2013.01); *A61F 2250/006* (2013.01)

(58) Field of Classification Search
CPC ................. A61F 2002/061; A61F 2002/826; A61F 2002/828; A61F 2002/821; A61F 2/064; A61F 2/856; A61F 2/854; A61F 2/852; A61B 2017/1135
USPC ................................................. 623/1.16, 1.35
See application file for complete search history.

(56) References Cited

U.S. PATENT DOCUMENTS

| | | | | |
|---|---|---|---|---|
| 5,354,308 | A * | 10/1994 | Simon et al. | 623/1.15 |
| 5,617,878 | A * | 4/1997 | Taheri | 128/898 |
| 6,652,567 | B1 * | 11/2003 | Deaton | 623/1.1 |
| 6,827,736 | B2 * | 12/2004 | Perouse | 623/1.36 |

(Continued)

OTHER PUBLICATIONS

International Search Report mailed on Apr. 13, 2012 for PCT international Application No. PCT/IL2010/001001.

*Primary Examiner* — Thomas J Sweet
*Assistant Examiner* — Cheryl Miller
(74) *Attorney, Agent, or Firm* — Pearl Cohen Zedek Latzer Baratz LLP

(57) ABSTRACT

A stent graft provides for a fenestration to be created by a side branch fenestration creation device. A kit comprises a side branch fenestration creation device and a stent graft in which a fenestration may be created thereby.

9 Claims, 3 Drawing Sheets

(56) References Cited

U.S. PATENT DOCUMENTS

| | | | | |
|---|---|---|---|---|
| 7,425,219 B2* | 9/2008 | Quadri | A61F 2/07 | 606/153 |
| 8,048,140 B2* | 11/2011 | Purdy | A61F 2/07 | 623/1.13 |
| 8,216,298 B2* | 7/2012 | Wright | A61F 2/07 | 623/1.13 |
| 2001/0010006 A1* | 7/2001 | Bachinski et al. | | 606/153 |
| 2002/0058897 A1* | 5/2002 | Renati | A61F 2/2493 | 604/8 |
| 2003/0176911 A1* | 9/2003 | Iancea | A61F 2/07 | 623/1.13 |
| 2004/0088007 A1* | 5/2004 | Eidenschink | A61F 2/856 | 607/1 |
| 2004/0204754 A1* | 10/2004 | Kaplan et al. | | 623/1.16 |
| 2005/0049680 A1* | 3/2005 | Fischell et al. | | 623/1.15 |
| 2005/0131517 A1 | 6/2005 | Hartley et al. | | |
| 2005/0171598 A1 | 8/2005 | Schaeffer | | |
| 2006/0025849 A1* | 2/2006 | Kaplan | A61F 2/91 | 623/1.15 |
| 2007/0142896 A1 | 6/2007 | Anderson et al. | | |
| 2008/0086193 A1* | 4/2008 | Thramann | | 623/1.13 |
| 2009/0105733 A1* | 4/2009 | Coleman | A61B 17/11 | 606/153 |
| 2009/0125097 A1* | 5/2009 | Bruszewski et al. | | 623/1.23 |
| 2009/0228020 A1 | 9/2009 | Wallace et al. | | |
| 2009/0234348 A1* | 9/2009 | Bruszewski et al. | | 606/33 |
| 2009/0240316 A1 | 9/2009 | Bruszewski | | |
| 2009/0264977 A1* | 10/2009 | Bruszewski et al. | | 623/1.11 |
| 2009/0264985 A1 | 10/2009 | Bruszewski | | |
| 2009/0264988 A1* | 10/2009 | Mafi et al. | | 623/1.23 |
| 2009/0264990 A1 | 10/2009 | Bruszewski | | |
| 2010/0106175 A1* | 4/2010 | McLachlan et al. | | 606/185 |
| 2010/0211163 A1* | 8/2010 | Gershlick | A61F 2/86 | 623/1.18 |
| 2011/0054586 A1* | 3/2011 | Mayberry et al. | | 623/1.11 |
| 2012/0041544 A1* | 2/2012 | Wolf | | 623/1.35 |
| 2012/0136385 A1* | 5/2012 | Cully | A61F 2/07 | 606/194 |
| 2012/0221090 A1* | 8/2012 | Wolf | A61F 2/07 | 623/1.11 |

* cited by examiner

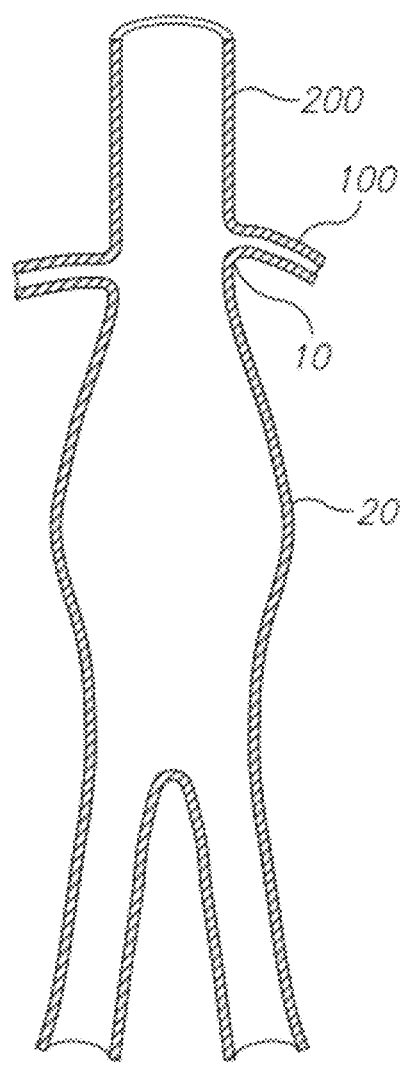
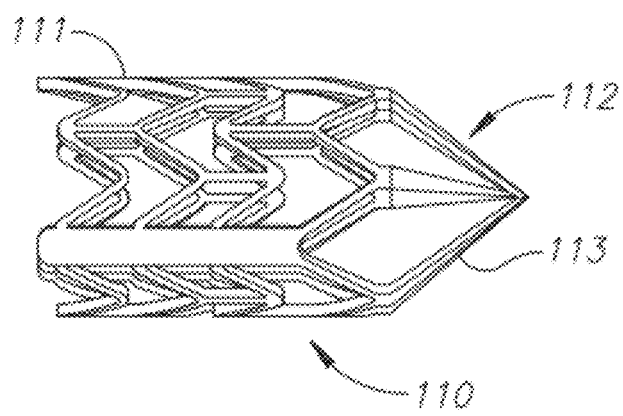
FIG.1
FIG.2

METHOD OF IMPLANTING A STENT GRAFT AND CREATING A FENESTRATION THEREIN

CROSS REFERENCE TO RELATED APPLICATIONS

This application is a continuation-in-part of PCT International Application No. PCT/IL2010/001001, international filing date Nov. 30, 2010, entitled "METHOD OF IMPLANTING A STENT GRAFT AND CREATING A FENESTRATION THEREIN", published on Jun. 3, 2011, as International Patent Application Publication No. WO 2011/064784, which claims priority from U.S. Provisional Application No. 61/264,843, filed Nov. 30, 2009; this application also claims the benefit of U.S. Provisional Patent Application No. 61/524,123, filed Aug. 16, 2011 and entitled "STENT GRAFT", all three of which applications are incorporated herein by reference in their entireties.

FIELD OF THE INVENTION

This invention is directed to a stent graft in which a fenestration may be formed, from the outside, by a side branch vessel fenestration creation device.

BACKGROUND OF THE INVENTION

An aneurysm is a localized, blood-filled balloon-like bulge of a blood vessel, caused by the weakening of the vessel wall. One type of aneurysm is an aortic aneurysm, which occurs in the main artery carrying blood from the left ventricle of the heart to the body. When the size of an aneurysm increases, there is a significant risk of rupture, resulting in severe hemorrhage, which may even lead to death. Aneurysms may be hereditary or caused by disease, either of which can lead to the weakening of the blood vessel wall.

For aneurysms in the aorta, arms, legs or head, the weakened section of the vessel may be replaced by a bypass graft that is sutured at the vascular stumps. Instead of sewing, the graft tube ends, which are made rigid and expandable by a nitinol wireframe, can be inserted into the vascular stumps and permanently fixed there by external ligature or an expandable ring. Less invasive endovascular techniques allow covered metallic stent grafts to be inserted through the arteries of the leg and deployed across the aneurysm.

Thus, when the aneurysm occurs in a region of a blood vessel where there is no branching leading to other blood vessels, stent grafts may be easily placed, thereby bypassing the aneurysm and highly reducing the risk of rupture. However, when the aneurysm occurs in the close vicinity of another blood vessel that branches off from the vessel with the aneurysm, it is sometimes impossible to place a stent graft without blocking the branch vessel. Such a condition occurs in approximately 40% of the patients diagnosed with an aortic aneurysm, wherein the length and diameter of the healthy vessel remaining between the aneurysm and the branch to the renal arteries, is insufficient to hold a stent graft in place. In such instances, stent grafts cannot be used, and certain patients are referred to invasive surgery. However, surgery is a relatively high risk procedure, and further, not all patients may be operated on, thus leaving a large number of patients with untreated, life threatening, aneurysms.

There are several published methods aiming at treating such aneurysms; however, they all suffer from various disadvantages.

One exemplary such method of treating such aneurysms is the preparation of a tailored stent graft, prepared according to the specific anatomy of the patient being treated. Such a tailored stent graft is prepared so that it includes openings at the branches, so as to allow blood to naturally flow from the main vessel into the side branch vessels. Such stent grafts are disclosed, e.g., in U.S. Patent Application Publication No. 2005/0171598. However, the preparation of such stent grafts is expensive and is time consuming, since each needs to be prepared specifically according to the anatomy of each treated patient. Further, the placement of such a tailored stent graft is relatively complicated, and therefore is a relatively long and high-risk procedure. Furthermore, such a procedure requires high expertise and is performed by only a very limited number of physicians.

Another method for treating such aneurysms is published in U.S. Patent Application Publication No. 2009/0240316 ("US '316"), although it is not known to be used in the art. According to the disclosure of US '316, a bloused stent-graft is deployed into a main vessel such that the bloused section of the bloused stent-graft covers the opening of a branch vessel emanating from the main vessel. The bloused section includes loose graft cloth, and a pressure differential between the main vessel and the branch vessel causes the bloused section to be forced into an ostium of the branch vessel, thereby creating a pocket aligned with the branch vessel. Further, according to US '316, a distal tip of a puncture device is located in the pocket and thus aligned with the branch vessel. An outward force is applied to the puncture device to cause the distal tip of the puncture device to puncture the bloused section, thus creating a collateral opening, or fenestration, in the bloused section precisely aligned with the branch vessel. However, it should be understood that the physician placing the stent graft monitors the placement thereof by following the blood flow. Therefore, once the bloused stent graft is placed, it would be impossible for the physician to see where the branching of the vessel is, since the blood flow has stopped. Therefore, it would be impossible, if not very difficult, to implement such a method as disclosed in US '316.

U.S. Patent Application Publication No. 2005/0131517 discloses a stent graft with a relatively flexible or variable fenestration, wherein the fenestration is placed at the branching vessel, and a branch vessel stent is placed in the branch vessel. However, it is questionable whether such a flexible fenestration would be able to fit the anatomy of any given patient.

As known in the art, similar difficulties are encountered when using stenting procedures for treating any endovascular conditions involving branching of the treated blood vessel. Such endovascular conditions include atherosclerotic vessel stenosis, iatrogenic stricture of a vessel, external pressure causing vessel lumen narrowing, aneurysmal dilatation, bleeding vessel, and any other condition that requires stenting of a bifurcated segment either by a dilating stent or a stent graft.

It would therefore be beneficial to develop a method by which a stent graft may be used effectively and efficiently, even in instances where the medical condition requiring stenting of a bifurcated segment occurs relatively close to a branching of the vessel.

SUMMARY OF THE INVENTION

As used herein, the term "close proximity of the branching of the main vessel" is understood to mean any medical condition requiring stenting of a bifurcated segment, such as an aneurysm atherosclerotic vessel stenosis, iatrogenic stricture of a vessel, external pressure causing vessel lumen narrowing, aneurysmal dilatation, bleeding vessel, that is close enough to the branching of the main vessel, so that it cannot be treated by conventional methods, e.g., using a stent graft, without blocking the blood flow to the side branch vessel. According to one embodiment, the medical condition requiring stenting of a bifurcated segment is considered to be too close to the branching of the main vessel when the distance between the two is approximately 13 mm or less.

The invention provides a stent graft in which a fenestration is created, from the outside, by the side branch vessel fenestration creation device. The invention further provides a kit comprising a side branch vessel fenestration creation device and a stent graft in which a fenestration is created by the side branch vessel fenestration creation device, once deployed in an artery.

The invention further provides a method for forming a fenestration through a stent graft at a location where a main vessel in which the stent graft is placed branches into a side branch vessel, wherein the method includes:
  a. placing a side branch vessel stent in the side branch vessel so that at least a portion of the side branch vessel stent protrudes into the lumen of the main vessel; and
  b. deploying the stent graft in the main vessel, so that:
    i. at least the portion of the side branch vessel stent punctures the stent graft at the location where the main vessel branches into the side branch vessel; or
    ii. the side branch vessel stent marks the location where the fenestration is to be formed, so that additional means may be inserted or may in advance have been inserted to aid in the creation of the fenestration.

The invention further provides a method for treating a medical condition in a main vessel that is in close proximity of the branching of the main vessel to a side branch vessel, including the following steps:
  a) placing a side branch vessel stent in the side branch vessel, so that at least a portion of the branch vessel stent protrudes into the lumen of the main vessel; and
  b) deploying a stent graft in the main vessel, whereby either:
    i) the stent graft is punctured by the side branch vessel stent from the outer side of the stent graft; or
    ii) a puncture point is marked in the stent graft by the side branch vessel stent and additional means are used to aid in puncturing the stent graft at the puncture point.

The invention additionally provides the use of a side branch vessel stent to treat a medical condition in a main vessel that is in close proximity of the branching of the main vessel to a side branch vessel, comprising
  a) placing a side branch vessel stent in the side branch vessel, so that at least a portion of side branch vessel stent protrudes into the lumen of the main vessel; and
  b) deploying a stent graft in the main vessel, whereby either:
    i) the stent graft is punctured by the side branch vessel stent from the outer side of the stent graft; or
    ii) a puncture point is marked in the stent graft by the side branch vessel stent and additional means are used to aid in puncturing the stent graft at the puncture point.

BRIEF DESCRIPTION OF THE DRAWINGS

Embodiments of the invention will be understood and appreciated more fully from the following detailed description in conjunction with the figures, which are not to scale, in which like reference numerals indicate corresponding, analogous or similar elements, and in which:

FIG. 1 shows an example of a blood vessel with an aneurysm in the proximity of branch vessels;

FIG. 2 shows a side branch vessel fenestration creation device according to some embodiments of the invention, in a closed configuration;

DETAILED DESCRIPTION OF THE INVENTION

Figure 4:
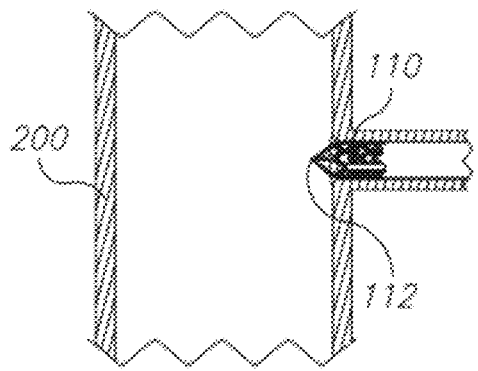
FIG. 4 shows the placement of side branch vessel fenestration creation device in branch vessel, according to some embodiments of the invention, in the closed configuration so that the side branch vessel fenestration creation device protrudes into the main vessel lumen.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The invention provides a method for creating a fenestration in a stent graft at the point where the main vessel, in which the stent graft is placed, branches into a side branch vessel. Reference is made to FIG. 1 (prior art), which describes an aneurysm 20 in a main vessel 200 that is close to the branching point 10 of the main vessel 200 and the side branch vessel 100.

According to this invention, prior to the deployment of the stent graft in the main vessel, a side branch vessel fenestration creation device is placed in the branch vessel so that the side branch vessel fenestration creation device protrudes into the lumen of the main vessel. Once the side branch vessel fenestration creation device is anchored within the side branch vessel, the stent graft is deployed in the main vessel. During the deployment, a fenestration in the stent graft is created by the side branch vessel fenestration creation device, from the outer side of the stent graft, thereby allowing blood to flow through the stent graft, through the side branch vessel fenestration creation device and into the side branch vessel. According to further embodiments, once the stent graft is deployed, a fenestration is created at the branching point of the vessel using a side branch vessel fenestration creation device and any additional appropriate means. According to this embodiment, the side branch vessel fenestration creation device marks the point where the fenestration is to be created, so that additional means may be inserted, or may in advance be inserted in order to aid in the creation of the fenestration.

According to an embodiment of the invention, the side branch vessel fenestration creation device has two configurations, the first referred to as the "closed configuration" and the second referred to as the "opened configuration". In one embodiment, the side branch vessel fenestration creation device is in an open configuration when at rest, and may be shaped into a closed configuration for insertion into a branch vessel. As will be described below, the side branch vessel fenestration creation device may be "released" from its closed configuration into its pre-shaped, open configuration at the appropriate time through the appropriate means.

It should be noted that, although the side branch vessel may not be in need of a stent to support its structure, as a typical stent would do, and although the side branch vessel fenestration creation device may not actually function as a stent within the side branch vessel to support its structure, the side branch vessel fenestration creation device may be referred to in the application as a stent, e.g., side branch vessel stent, due to its placement within the side branch vessel of the main vessel.

According to this embodiment, the side branch vessel fenestration creation device is placed in the branch vessel in the closed configuration, such that at least a portion of it protrudes into the lumen of the main vessel. When the stent graft is deployed in the main vessel, a portion of the side branch vessel fenestration creation device in the closed configuration punctures the stent graft, thereby enabling the creation of a fenestration in the stent graft at the point of branching of the blood vessel, thus allowing blood to continue its flow between the main vessel and the side branch vessel. According to further embodiments, any appropriate means may be used to puncture the stent graft together with the side branch vessel fenestration creation device. According to further embodiments, the side branch vessel fenestration creation device marks the point where the fenestration is to be created, so that additional means may be inserted or may in advance be inserted in order to aid in the creation of the fenestration.

According to one embodiment, once a fenestration is formed through the stent graft at the branching point of the vessel, the configuration of the side branch vessel fenestration creation device is changed to an opened configuration. According to one embodiment, the configuration of the side branch vessel fenestration creation device is changed to the opened configuration by means of release of a mechanical lock, thus enabling the side branch vessel fenestration creation device to obtain a pre-shaped opened configuration. According to one embodiment, the side branch vessel fenestration creation device changes its configuration to the opened configuration through the application of heat or by any other appropriate means. The heat may be applied by a catheter inserted into the vessel, or by any other appropriate means.

Reference is now made to FIG. 2, which describes one embodiment of the side branch vessel fenestration creation device 110 in its closed configuration. According to this embodiment, the side branch vessel fenestration creation device 110 includes two regions, the side branch vessel fenestration creation device body 111 and the side branch vessel fenestration creation device tip 112. According to this embodiment, the side branch vessel fenestration creation device body 111 is tubular shaped and is placed in the side branch vessel. According to further embodiments, the side branch vessel fenestration creation device body 111 is of any other appropriate shape suitable to be placed in the side branch vessel.

Additionally, the side branch vessel fenestration creation device body 111 may include any appropriate means for anchoring the side branch vessel fenestration creation device 110 in the side branch vessel (not shown in figure). For example, the side branch vessel fenestration creation device body may include struts directed outwardly that will rest against the main vessel wall around the branched vessel ostium. According to one embodiment, the side branch vessel fenestration creation device 110 is anchored in the side branch vessel in the closed configuration, and remains anchored therein also when changed to the opened configuration.

The side branch vessel fenestration creation device tip 112 is cone shaped in the closed configuration, as shown in FIG. 2. According to other embodiments (not shown in the figures), the side branch vessel fenestration creation device tip 112 has the shape of a tetrahedron in the closed configuration when viewed from the end. According to the invention, the side branch vessel fenestration creation device tip 112 may be of any appropriate shape in the closed configuration that enables the formation of a fenestration through the stent graft at the branching point of the blood vessel. According to one embodiment, the side branch vessel fenestration creation device tip 112 comprises more than one finger 113, which form the shape of the closed configuration of the side branch vessel fenestration creation device tip, i.e., a cone, tetrahedron, etc. According to certain embodiments, the configuration of the fingers 113 is symmetrical, while according to other embodiments, it is not.

Figure 3:
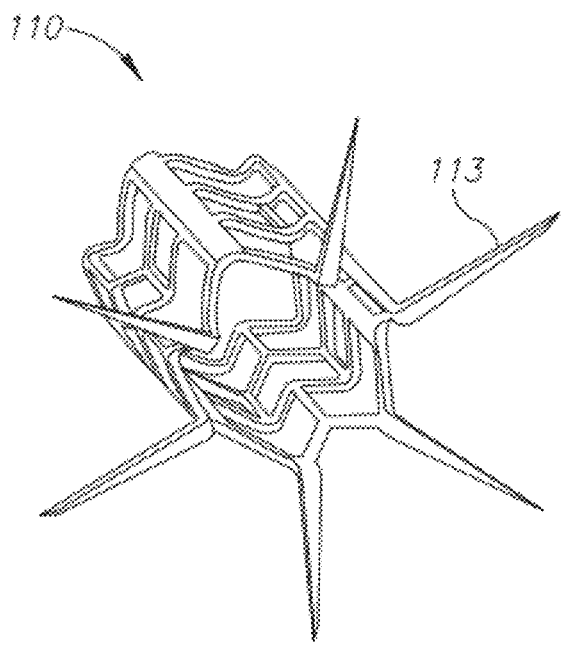
FIG. 3 shows the side branch vessel fenestration creation device, according to some embodiments of the invention, in a opened configuration.

Reference is now made to FIG. 3, which describes one embodiment of the opened configuration of side branch vessel fenestration creation device 110. According to this embodiment, the side branch vessel fenestration creation device tip changes from a cone shape to a "sun-like" shape composed of several finger-like projections (or fingers) 113 that are spread out. According to this embodiment, the fingers 113 serve the purpose of abutting the stent graft and the side wall of the main vessel, around the opening of the side branch vessel, so that the stent graft and the side wall of the main vessel remain touching one another around the fenestration. The number of fingers 113 may be any appropriate number in order to fulfill this purpose. According to one embodiment, the number of fingers is between three and ten. According to another embodiment, the number of fingers 113 is between five and nine. According to another embodiment, the number of fingers 113 is between six and eight. According to another embodiment, the number of fingers 113 is six.

According to the invention, any other means may also be used for causing the stent graft to abut the side wall of the main vessel, around the opening of the side branch vessel, so that the stent graft and the side wall of the main vessel remain touching one another around the fenestration. According to one embodiment, mechanical force may be applied from within the main stent graft so as to ensure that the stent graft and the side wall of the main vessel remain touching one another around the fenestration.

According to the invention, the side branch vessel fenestration creation device may be prepared from any appropriate composition, such as nitinol. According to one embodiment, the nitinol side branch vessel fenestration creation device is at, or is close to, the phase transformation between austenitic and martensitic phases so that it will be completely transformed to the austenitic phase when heat (e.g., at a temperature range of approximately 38-45° C.) is applied to it. According to further embodiments, the side branch vessel fenestration creation device may be formed of nitinol at more than one transformation phase. According to certain embodiments, the side branch vessel fenestration creation device body 111 is made of nitinol at the fully austenitic phase, while the side branch vessel fenestration creation device tip 112 is made of nitinol at a different metallurgic phase, such as the martensitic phase. According to further embodiments, the side branch vessel fenestration creation device tip 112 is set at a metallurgic phase that is not fully martensitic and not fully austenitic.

Figure 5:
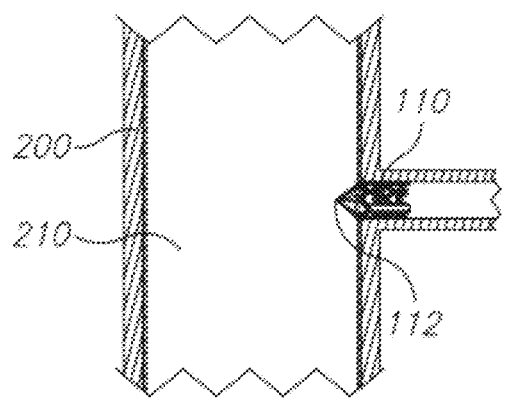
FIG. 5 shows the deployment of the stent graft in the main vessel, wherein a fenestration of the stent graft has been created by the side branch vessel fenestration creation device at the side branch vessel opening.
Figure 6:
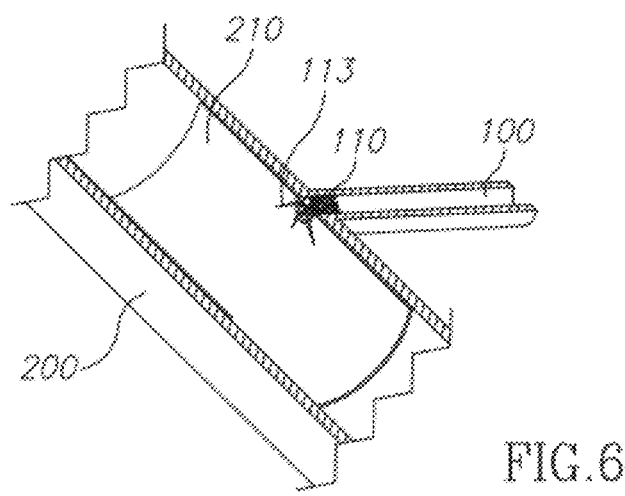
FIG. 6 shows a cross section of the final configuration of the main vessel supported by the stent graft, wherein a fenestration of the stent graft has been created by the side branch vessel fenestration creation device, shown in its opened configuration.

As shown in FIG. 4, the side branch vessel fenestration creation device 110 is placed in the side branch vessel 100 and set therein in such a way that the side branch vessel fenestration creation device tip 112 in its closed configuration protrudes into the lumen of the main vessel 200. Then, as depicted in FIG. 5, once the stent graft 210 is deployed in the main vessel 200, the tip 112 of the side branch vessel fenestration creation device 110 protrudes into and creates a fenestration in the wall of the stent graft 210. Subsequently, as described in FIG. 6, the side branch vessel fenestration creation device 110 is further transformed into its opened configuration, thus spreading fingers 113 and anchoring the stent graft 210 to the side wall of the main vessel 200, around the opening of the side branch vessel 100.

The invention further includes a method for treating a medical condition in a main vessel that is in close proximity of the branching of the main vessel, including the following steps:
  a) placing a side branch vessel fenestration creation device in the side branch vessel, so that an end thereof protrudes into the lumen of the main vessel; and
  b) deploying a stent graft in the main vessel,
whereby the end of the side branch vessel fenestration creation device protrudes into and punctures the stent graft from the outer side of the stent graft, thereby creating a fenestration therethrough.

According to further embodiments, once the stent graft is deployed, a fenestration is created at the branching point of the vessel using the side branch vessel fenestration creation device and any additional appropriate means. According to further embodiments, the side branch vessel fenestration creation device marks the point where the fenestration is to be created, so that additional means may be inserted to aid in the creation of the fenestration.

According to some embodiments of the invention, the method of this invention further includes means of anchoring the side branch vessel fenestration creation device in the side branch vessel. According to further embodiments, the method of this invention further includes means of causing the stent graft to abut the side wall of the main vessel around the opening of the side branch vessel, so that the stent graft and the side wall of the main vessel remain touching one another around the fenestration.

This invention further includes the use of a side branch vessel fenestration creation device to treat a medical condition in a main vessel that is in close proximity of the branching of the main vessel, comprising
  a) placing a side branch vessel fenestration creation device in the side branch vessel, so that an end thereof protrudes into the lumen of the main vessel; and
  b) deploying a stent graft in the main vessel,
whereby the end of the side branch vessel fenestration creation device protrudes into a punctures the stent graft from the outer side of the stent graft, thereby creating a fenestration therethrough.

According to further embodiments, once the stent graft is deployed, a fenestration is created at the branching point of the vessel using the side branch vessel fenestration creation device and any additional appropriate means. According to further embodiments, the side branch vessel fenestration creation device marks the point where the fenestration is to be created, so that additional means may be inserted to aid in the creation of the fenestration.

According to some embodiments, the use of a side branch vessel fenestration creation device to treat an aneurysm that is in close proximity of the branching of the main vessel further includes means of anchoring the side branch vessel fenestration creation device in the side branch vessel. According to further embodiments, the use of a side branch vessel fenestration creation device to treat an aneurysm that is in close proximity of the branching of the main vessel further includes means of causing the stent graft to abut the side wall of the main vessel around the opening of the side branch vessel, so that the stent graft and the side wall of the main vessel remain touching one another around the fenestration.

The invention is further directed to a stent graft in which a fenestration may be formed, from the outside, by a side branch vessel fenestration creation device. Further, once the fenestration is formed it is sealed by the side branch vessel fenestration creation device, by means of the stent graft itself, or by a combination thereof, so as to minimize blood leaks from around the fenestration back into the blood vessels.

It should be understood that all of the embodiments detailed herein, relating to characteristics of the stent graft, are meant to include stent grafts in which only a region, several regions, a portion, several portions, an extension or several extensions thereof have the defined characteristics.

According to some embodiments of the invention, the stent graft is prepared from materials that enable the side branch vessel fenestration creation device to create a fenestration, from the outside, in the stent graft. According to some embodiments, the stent graft is prepared from Teflon derivatives such as ePTFE, PTFE, or any combination thereof. According to further embodiments, the stent graft is prepared from nitinol. According to further embodiments, the stent graft is prepared from nitinol coated with Teflon derivatives such as ePTFE, PTFE, or any combination thereof.

According to further embodiments, the side wall of the stent graft is thin, so as to enable the side branch vessel fenestration creation device to create a fenestration, from the outside, in the stent graft. According to some embodiments, the thickness of the side wall of the stent graft is less than 0.05 mm. According to further embodiments, the thickness of the side wall of the stent graft is less than 0.08 mm. According to further embodiments, the thickness of the side wall of the stent graft is less than 0.1 mm. According to further embodiments, the thickness of the side wall of the stent graft is less than 0.03 mm.

According to further embodiments, the side wall of the stent graft is inelastic, so as to enable the side branch vessel fenestration creation device to create a fenestration, from the outside, in the stent graft.

Figure 7:
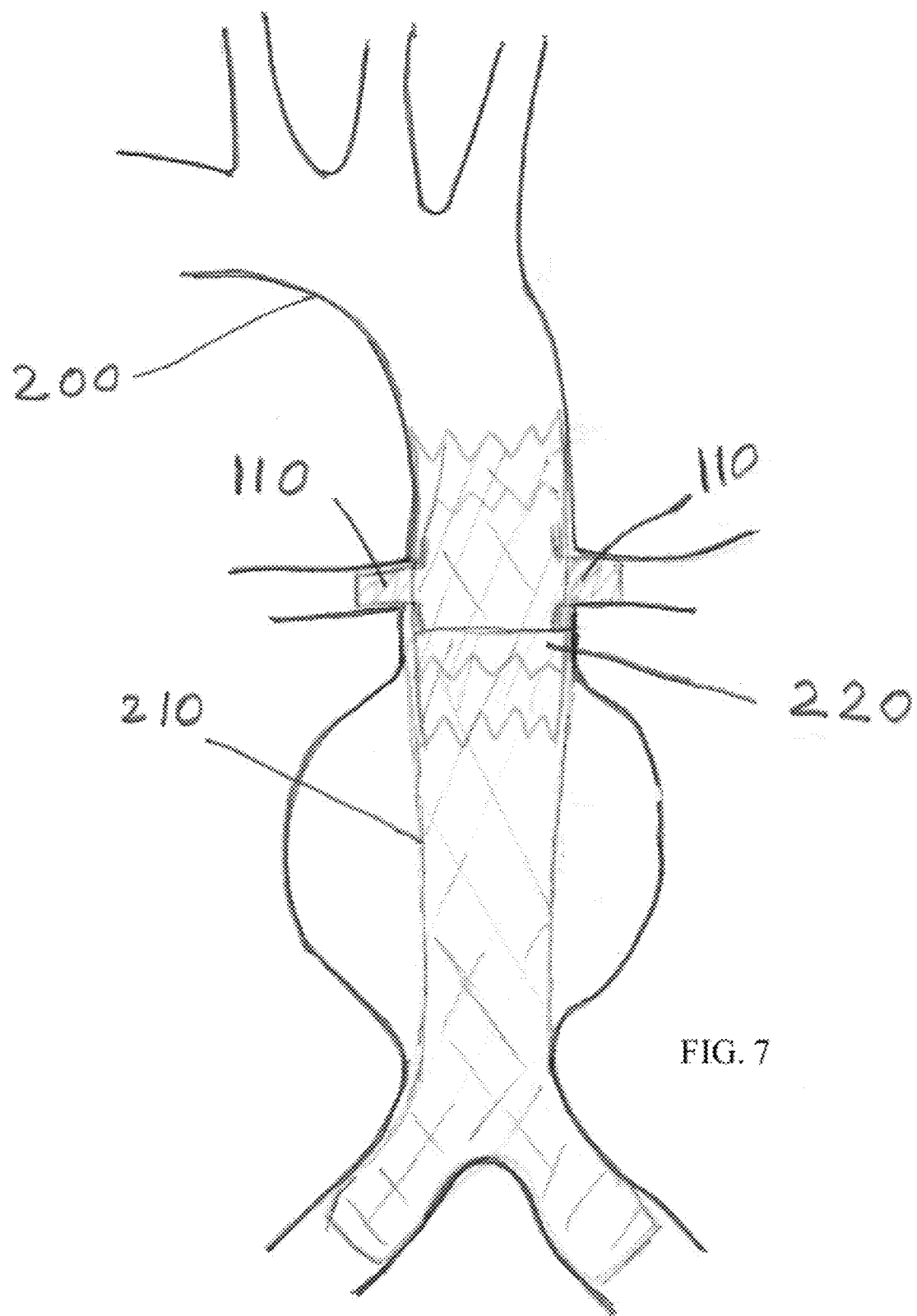
FIG. 7 shows a cross section of the final configuration of the main vessel supported by the stent graft, wherein two fenestrations of the stent graft have been created by two separate side branch vessel fenestration creation devices and wherein the stent graft includes a region that is designed so that a fenestration may be formed, from the outside, by the side branch vessel fenestration creation devices.

Reference is made to FIG. 7, which shows a cross section of the final configuration of the main vessel (200), which, according to an embodiment of the invention is supported by stent graft (210), wherein two fenestrations of stent graft (210) have been created by two separate side branch vessel fenestration creation devices (110). Stent graft (210) includes a region (220) that is designed so that a fenestration may be formed, from the outside, by the side branch vessel fenestration creation devices (110). According to further embodiments, at least one fenestration in stent graft (210) is created by at least one side branch vessel fenestration creation device (110). According to further embodiments, two fenestrations in stent graft (210) are created by two separate side branch vessel fenestration creation devices (110).

The invention, in some embodiments, is further directed to a kit comprising a side branch vessel fenestration creation device and a stent graft in which a fenestration may be created by the side branch vessel fenestration creation device. According to some embodiments, the kit comprises any known stent graft in which a fenestration may be created by the side branch vessel fenestration creation device. According to further embodiments, the kit comprises a stent graft specifically designed so that a fenestration may be created therein by the side branch vessel fenestration creation device, including any stent graft disclosed herein.

Various aspects of the invention are described in greater detail in the following Examples, which represent embodiments of this invention, and are by no means to be interpreted as limiting the scope of this invention.

The invention claimed is:

1. A method for treating a medical condition in a main vessel that is in close proximity of a branching of the main vessel to a side branch vessel, including the following steps:
   placing a side branch vessel stent in the side branch vessel, so that at least a portion of said side branch vessel stent protrudes into the lumen of the main vessel; and
   deploying a stent graft in the main vessel after placing said side branch vessel stent in said side branch vessel,
   so that at least part of said portion of the side branch vessel stent that protrudes into the lumen of the main vessel punctures the stent graft, and wherein the side branch vessel stent is transformed from a closed configuration to an opened configuration after the at least part of said portion of the side branch vessel stent punctures the stent graft.

2. A method for forming a fenestration through a stent graft at a location where a main vessel, in which said stent graft is placed, branches into a side branch vessel, said method including:
   placing a side branch vessel stent in said side branch vessel so that at least a portion of said side branch vessel stent protrudes into the lumen of said main vessel; and
   deploying the stent graft in the main vessel after placing said side branch vessel stent in said side branch vessel, so that at least said portion of the side branch vessel stent punctures the stent graft at the location where the main vessel branches into the side branch vessel;
   wherein the side branch vessel stent has both a closed and an opened configuration; and
   wherein the side branch vessel stent is transformed from the closed configuration to the opened configuration after a fenestration is formed through the stent graft by way of the side branch vessel stent.

3. The method according to claim 2, wherein the side branch vessel stent includes a body region and a tip region.

4. The method according to claim 3, wherein the body region is tubular and includes means for anchoring the side branch vessel stent into the side branch vessel.

5. The method according to claim 3, wherein the tip region is conical in a closed configuration.

6. The method according to claim 3, wherein the tip region comprises several finger-like projections.

7. The method according to claim 1, wherein the opened configuration of the side branch vessel stent includes several spread out finger-like projections, which anchor the stent graft to the main vessel around where said main vessel branches into the side branch vessel.

8. The method according to claim 7, wherein the several spread out finger-like projections include six spread out finger-like projections.

9. The method according to claim 1, wherein the side branch vessel stent is prepared from nitinol.

* * * * *